United States Patent
Ruiter et al.

(10) Patent No.: US 11,781,946 B2
(45) Date of Patent: Oct. 10, 2023

(54) SYSTEMS AND METHODS OF PARALLEL TESTING OF MEDICAL DEVICES

(71) Applicant: PRONK TECHNOLOGIES, INC., Sun Valley, CA (US)

(72) Inventors: Karl A. Ruiter, Honolulu, HI (US); Gregory Randolph Alkire, Keene, CA (US); Julio Roberto Castro, Santa Clarita, CA (US); Robert Edward Whitten, Tujunga, CA (US)

(73) Assignee: PRONK TECHNOLOGIES, INC., Sun Valley, CA (US)

( * ) Notice: Subject to any disclaimer, the term of this patent is extended or adjusted under 35 U.S.C. 154(b) by 449 days.

(21) Appl. No.: 17/032,887

(22) Filed: Sep. 25, 2020

(65) Prior Publication Data
US 2021/0096043 A1    Apr. 1, 2021

Related U.S. Application Data

(60) Provisional application No. 62/907,515, filed on Sep. 27, 2019.

(51) Int. Cl.
*G16H 15/00*     (2018.01)
*G16H 40/40*     (2018.01)
*G01M 99/00*     (2011.01)

(52) U.S. Cl.
CPC .......... *G01M 99/005* (2013.01); *G16H 15/00* (2018.01); *G16H 40/40* (2018.01)

(58) Field of Classification Search
CPC .... G01M 99/005; G01M 99/00; G16H 15/00; G16H 40/40; G16H 40/00
See application file for complete search history.

(56) References Cited

U.S. PATENT DOCUMENTS

| | | | | |
|---|---|---|---|---|
| 2013/0268285 A1* | 10/2013 | Backes | ................. | G16H 40/40 702/183 |
| 2015/0147736 A1* | 5/2015 | Mathur | ................. | G09B 23/28 434/262 |
| 2015/0300923 A1* | 10/2015 | Halbert | .................... | G07C 3/00 702/122 |
| 2018/0211508 A1* | 7/2018 | Alkire | ................. | G08B 21/185 |
| 2018/0286510 A1* | 10/2018 | Kwan | .................... | G06Q 10/20 |

* cited by examiner

*Primary Examiner* — Mohamed Charioui
(74) *Attorney, Agent, or Firm* — Concept IP LLP; Pejman Yedidsion

(57) ABSTRACT

Systems, devices, and methods for testing medical devices comprising: a test device configured for testing a medical device; and a user computing device in communication with the test device, where the user computing device comprises a processor having addressable memory, where the processor is configured to: receive an ID of the medical device to be tested; select a profile associated with the received ID of the medical device; select a preset associated with the selected profile; initiate testing of the medical device by the test device; receive one or more parameter values from based on test information results from the test device; determine a test result based on pass criteria from a comparison of the received one or more parameter values to the one or more simulation parameter values of the preset.

18 Claims, 13 Drawing Sheets

FIG. 3

SYSTEMS AND METHODS OF PARALLEL TESTING OF MEDICAL DEVICES

CROSS-REFERENCE TO RELATED APPLICATIONS

This application claims priority to and the benefit of U.S. Provisional Patent Application No. 62/907,515, filed Sep. 27, 2019, the contents of which are hereby incorporated by reference herein for all purposes.

TECHNICAL FIELD

Embodiments relate generally to medical devices, and more particularly to testing of medical devices.

BACKGROUND

Medical devices must be regularly tested to ensure the safety of these medical devices. Manually testing a medical device may be time consuming and prone to errors. The requirements for testing of medical devices may vary based on whether a medical device will have contact with a patient or not.

SUMMARY

A system embodiment may include: a test device configured for testing a medical device; and a user computing device in communication with the test device, where the user computing device comprises a processor having addressable memory, where the processor is configured to: receive an ID of the medical device to be tested; select a profile associated with the received ID of the medical device, where the selected profile comprises one or more tests to run with the test device on the medical device; select a preset associated with the selected profile, where the selected preset sets one or more simulation parameter values in parallel so the medical device may perform capture and analysis of simulated parameters in parallel; initiate testing of the medical device by the test device; receive one or more parameter values from based on test information results from the test device; determine a test result based on pass criteria from a comparison of the received one or more parameter values to the one or more simulation parameter values of the preset.

A system embodiment for testing medical devices may include: a test device configured for testing a medical device; and a user computing device in communication with the test device, where the user computing device comprises a processor having addressable memory, where the processor may be configured to: receive an ID of the medical device to be tested; select a profile associated with the received ID of the medical device, where the selected profile comprises one or more tests to execute with the test device on the medical device; select a preset associated with the selected profile, where the selected preset sets two or more simulation parameter values in parallel thereby the medical device performs, capture and analysis of simulated parameters in parallel; initiate testing of the medical device by the test device; receive one or more parameter values from the test device based on test information results; and determine a test result based on pass criteria, where the determination may be based on a comparison of the received one or more parameter values to the one or more simulation parameter values of the preset.

In additional system embodiments, the test device further comprises a transceiver for communicating with the user computing device. In additional system embodiments, initiating testing of the medical device by the test device further comprises simulating a patient's vital signs. In additional system embodiments, the simulated patient vital signs comprise at least one of: temperature, cardiac output (CO), heart rate (HR), SpO2, RR, IBP-S, IBP-D, NBP-S, and NBP-D.

In additional system embodiments, the pass criteria may be based on a location of the medical device to be tested. In additional system embodiments, the location of the medical device to be tested may be in at least one of: an area near patients and an area away from patients. In additional system embodiments, receiving the ID of the medical device to be tested comprises the processor being further configured to: perform an optical scan of a unique identifier corresponding to the ID of the medical device to be tested, where the unique identifier comprises at least one of: a barcode and a QR code. In additional system embodiments, at least one test of the one or more tests to run of the selected profile may be an electrical safety test. In additional system embodiments, the selected profile may be a new profile. In additional system embodiments, the processor may be further configured to: display the determined test result on a user interface of the user computing device.

In additional system embodiments, the processor may be further configured to: generate a report based on the determined test result. In additional system embodiments, the generated report further comprises: identifying information of the tested medical device and a calibration date of the tested medical device. In additional system embodiments, the generated report further comprises: the selected profile, a time and date the testing of the medical device was initiated, the received one or more parameter values, a pass criteria for each test, and a fail criteria for each test.

Additional system embodiments may further include: a remote server having a processor with addressable memory, where the remote server may be in communication with the user computing device, where the processor of the remote server may be configured to: receive the generated report; and store the generated report. In additional system embodiments, the processor may be further configured to: capture an image of the received one or more parameter values on a display of the medical device. In additional system embodiments, the processor may be further configured to: generate an alert notification if the received one or more parameter values are entered faster than a predetermined limit thereby avoiding user error. In additional system embodiments, the processor may be further configured to: generate an alert notification if the received one or more parameter values are within a predetermined limit of one or more default simulation parameter values thereby avoiding user error.

A method embodiment may include: receiving, by a user computing device having a processor and addressable memory, an ID of the medical device to be tested, where the user computing device may be in communication with a test device configured for testing a medical device; selecting, by the processor of the user computing device, a profile associated with the received ID of the medical device, where the selected profile comprises one or more tests to run with the test device on the medical device; selecting, by the processor of the user computing device, a preset associated with the selected profile, where the selected preset sets one or more simulation parameter values in parallel thereby the medical device performs capture and analysis of simulated parameters in parallel; initiating, by the processor of the user computing device, testing of the medical device by the test device; receiving, by the processor of the user computing device, one or more parameter values based on test information results from the test device; and determining, by the processor of the user computing device, a test result based on pass criteria from a comparison of the received one or more parameter values to the one or more simulation parameter values of the preset.

Additional method embodiments may include: generating, by the processor of the user computing device, a report based on the determined test result, where the generated report comprises: identifying information of the tested medical device, a calibration date of the tested medical device, the selected profile, a time and date the testing of the medical device was initiated, the received one or more parameter values, a pass criteria for each test, and a fail criteria for each test. Additional method embodiments may include: generating, by the processor of the user computing device, an alert notification if the received one or more parameter values are entered faster than a predetermined limit to avoid user error. generating, by the processor of the user computing device, an alert notification if the received one or more parameter values are within a predetermined limit of one or more default simulation parameter values to avoid user error.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which:

FIG. 3 depicts a display of the user computer device of FIG. 2 configured for recognizing a test device;

DETAILED DESCRIPTION

Figure 1:
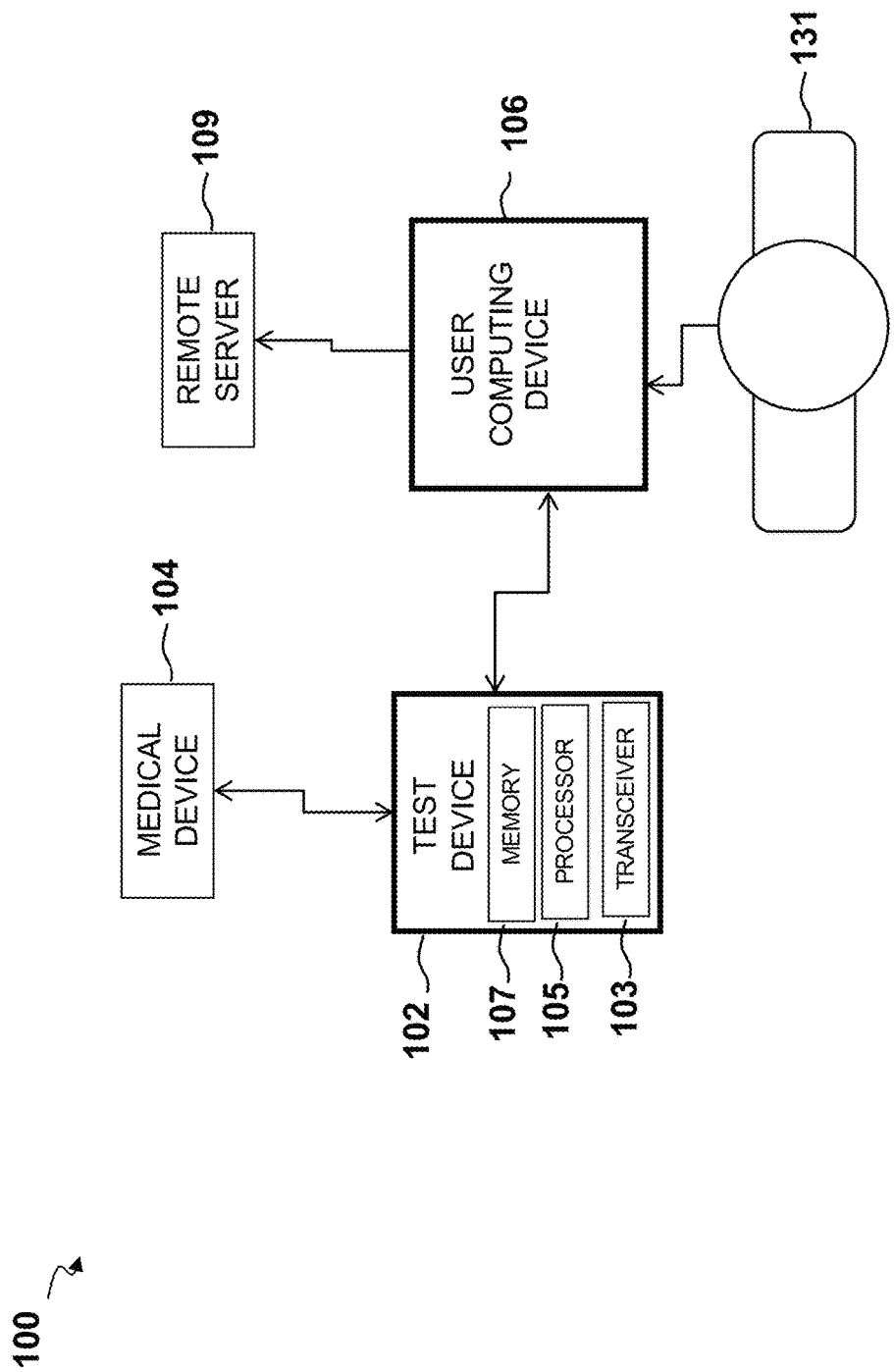
FIG. 1 depicts a block diagram of a system for testing medical devices.

With respect to FIG. 1, a system 100 for testing medical devices is shown. In one embodiment, a test device 102 may allow for generating parameter values indicating the result of one or more diagnostic tests of the performance of a medical device 104. The test device 102 may comprise a transceiver 103 and a processor 105. In some embodiments, the transceiver 103 may be a receiver and/or a transmitter. The processor 105 may have an addressable memory 107 and may execute and/or run one or more diagnostic tests for determining parameter values related to aspects of the medical device 104, such as temperature, cardiac output (CO), heart rate (HR), blood pressure (BP), $S_pO_2$, RR, IBP-S, IBP-D, NBP-S, NBP-D, and the like.

The test device 102 may be configured to run a plurality of safety tests on the medical device 104 to be tested. The kind, type, and criteria for each device may also differ based on the area of use. Devices in operating rooms may have different tests and corresponding pass or fail criteria than devices that are not located in patient areas. The test device 102 may be equipped to perform each safety test individually or to perform a number of tests sequentially. In one embodiment, the test device 102 may simulate a patient's vital signs in order to test the associated medical device 104. Each medical device 104 to be tested may have a different profile, where the profile is a set of tests to be run on a particular device and the corresponding pass or fail criteria for each test. The kind, type, and criteria for each device may also differ based on the area of use. Devices in operating rooms may have different tests and corresponding pass or fail criteria than devices that are not located in patient areas. The test device 102 may be equipped to perform each safety test individually or to perform a number of tests sequentially.

Figure 2:
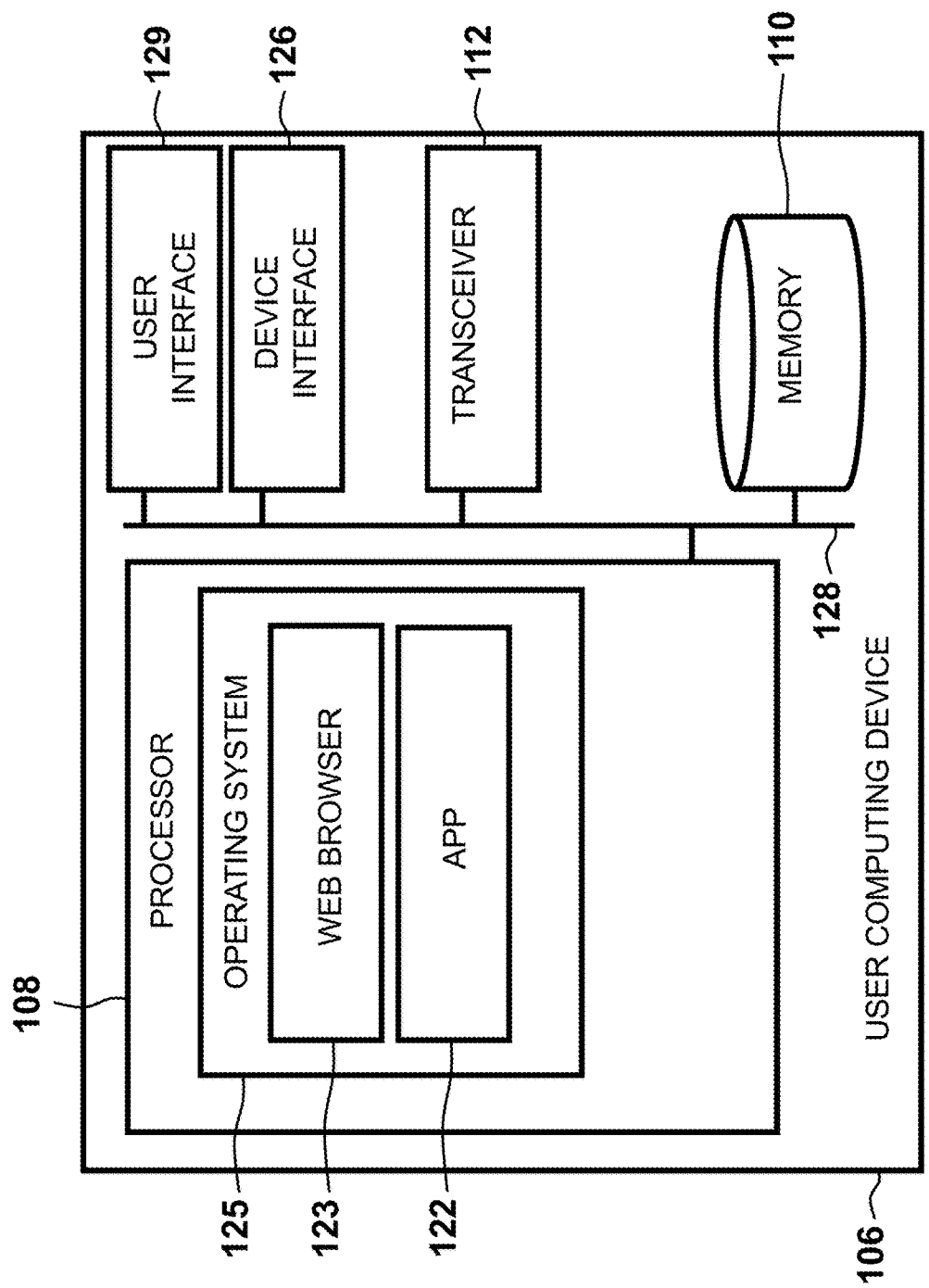
FIG. 2 depicts a top-level functional diagram of a user computing device.

In one embodiment, a user computing device 106 operated by a user 131 is configured for wireless communication with the test device 102. More specifically, and with respect to FIG. 2, an example of a top-level functional block diagram of the computing device 106 is shown. The computing device 106 comprises a processor 108, such as a central processing unit (CPU), addressable memory 110, an external device interface 126, e.g., an optional universal serial bus port and related processing, and/or an Ethernet port and related processing, and an optional user interface 129, e.g., an array of status lights and one or more toggle switches, and/or a display, and/or a keyboard and/or a pointer-mouse system and/or a touch screen. Optionally, the addressable memory may, for example, be: flash memory, eprom, and/or a disk drive or other hard drive. These elements may be in communication with one another via a data bus 128. In some embodiments, via an operating system 125 such as one supporting a web browser 123 and applications 122, the processor 108 may be configured to execute steps of a process establishing wireless communication with the test device 102 via a transceiver 112 of the computing device 106. In one embodiment, the transceiver 112 is a Bluetooth transceiver. In one embodiment, the user computing device 106 is a mobile device, such as a smartphone. In another embodiment, the user computing device 106 is a laptop computing device, a tablet, a smartphone, or the like. With respect to FIG. 1, the user computing device 106 may receive test results from the test device 102 and/or control aspects of the test device 102. Information regarding the test results as well as other information related to the one or more tests may be stored at the computing device 106 or at a remote server 109 in communication with the user computing device 106 and/or the test device 102.

Figure 3:
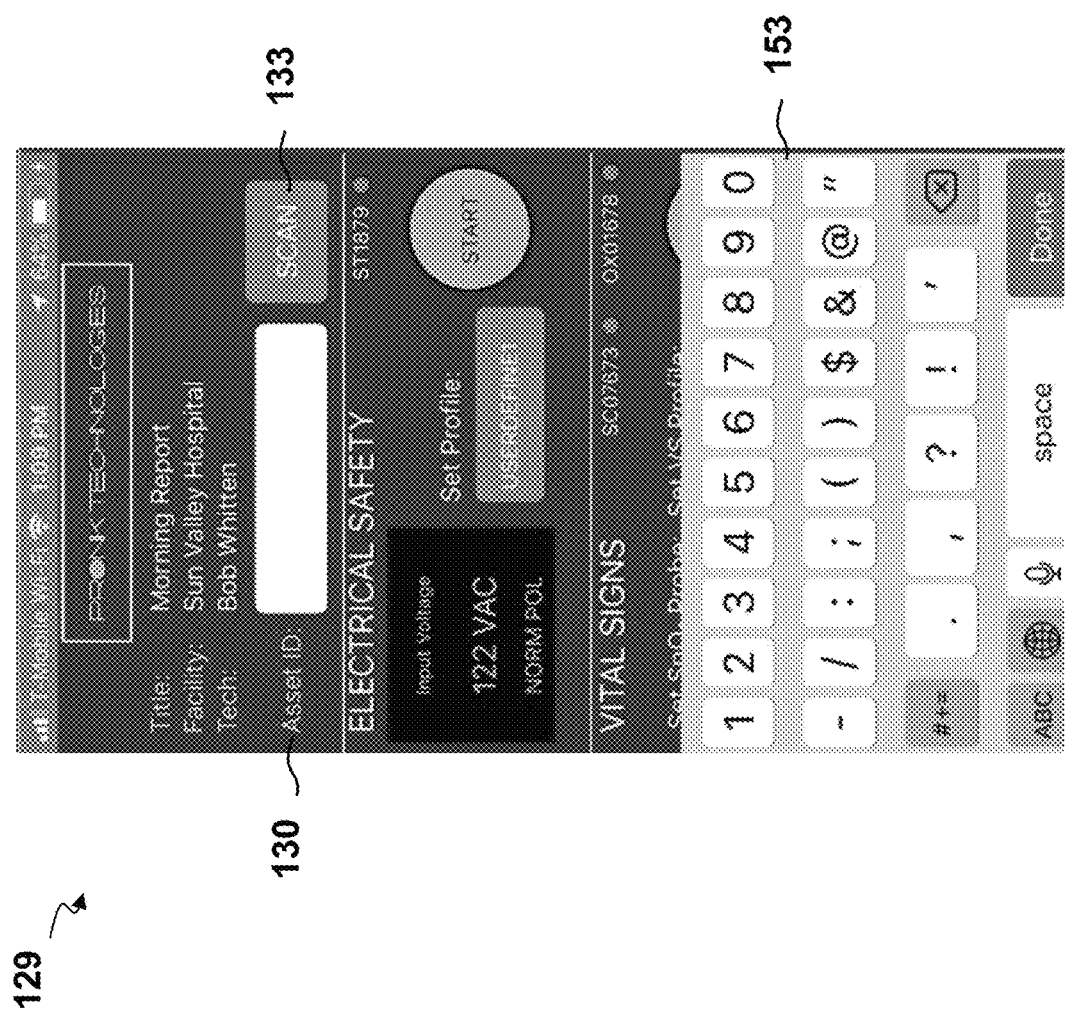

With respect to FIG. 3, a user 131 of FIG. 1 may interact with the user computing device 102 of FIG. 1 through a user interface 129. In one embodiment, the user 131 may wish to perform an electrical safety test of a medical device, such as medical device 104 of FIG. 1 with a test device, such as test device 102 of FIG. 1. The user may push a scan button 133. The processor 124 in turn executes steps for a camera of the user device 131 to perform an optical scan of a unique identifier of the medical device 104, such as a barcode, QR code, or the like. The unique identifier of the medical device 104 provides the user computing device with a unique asset ID 130 of the medical device 104. In another embodiment, the user 131 may enter the ID 130 manually with a touch keyboard 153.

Figure 4:
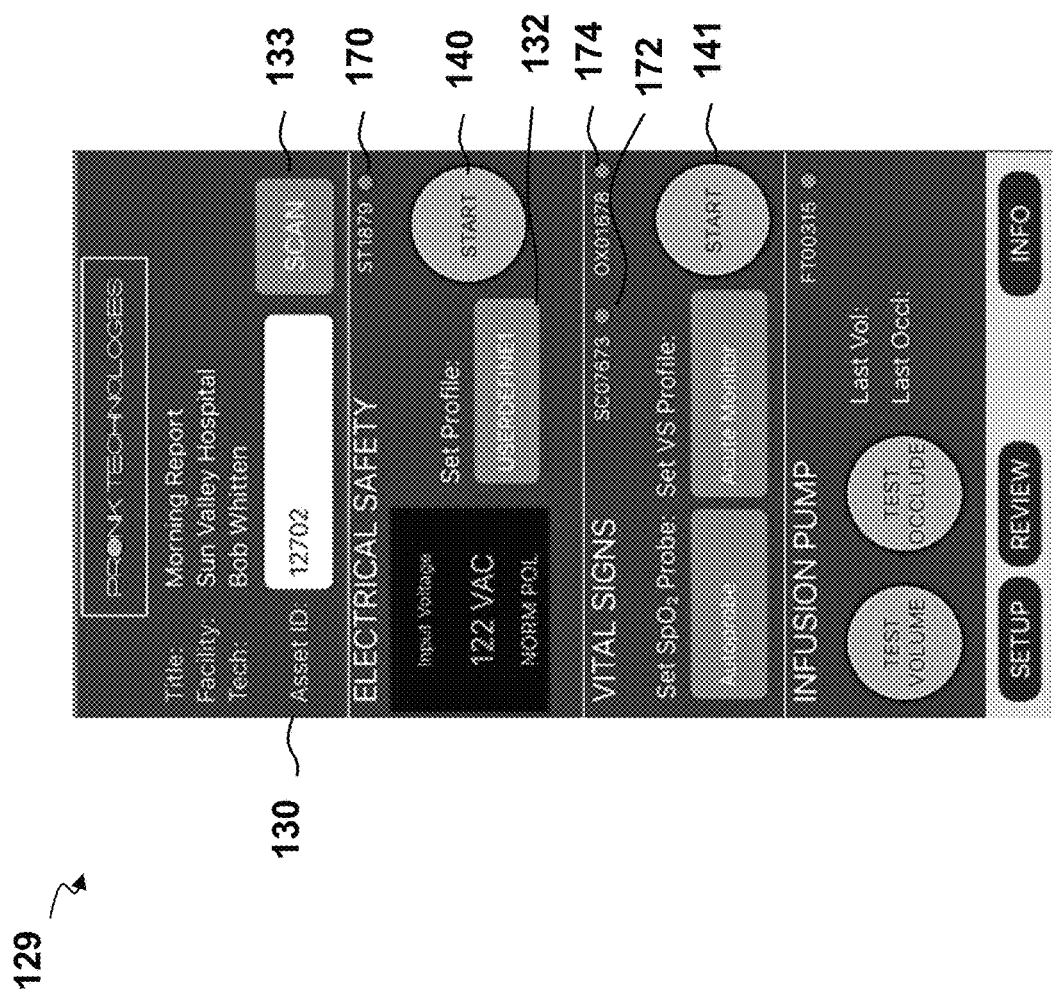
FIG. 4 depicts the display of FIG. 3 configured initializing a test to be performed by a test device.

With respect to FIG. 4, the user 131 may then select a profile 132. In one embodiment the profile 132 may be one or more series of tests to run with the test device 102 on the medical device 104. The one or more profiles 132 may be a preset list of tests or a user-defined set of tests to be run, such as one or more electrical safety tests. The user 131 may proceed to a new profile by selecting the profile 132 and further selecting a new profile from a pop-up list (not shown) displayed by selecting the profile 132.

The user 131 may then initiate the tests by selecting a start button 140. Selection of the start button 140 causes the processor to execute steps of instructions to generate a profile of tests to be wirelessly transmitted via the transceiver 112 and/or via a physical connection to the test device 102. The processor 105 of the test device 102 may then execute steps to run the profile of tests on the medical device 104. In one embodiment, upon completion of the tests, the test device 102 may determine results of the test and whether the results indicated a pass or fail result. In another embodiment, the user computing device 106 may determine a pass or fail result based on the test results determined by the test device 102. In another embodiment, the test results may be manually entered at the computing device 106 and a pass or fail result may be based on pass or fail criteria defined by the user 131 or established by the selected profile. This embodiment will be discussed in further detail below.

The result may then be transmitted back to the user computing device 106 to be displayed on the user interface 129. In one embodiment, and with respect to FIG. 5, a pass result 142 may be displayed on the user interface 129. In another embodiment, a fail result may be displayed. The user 131 may then review a generated report 144 (see FIG. 6) related to the tests performed by selecting a review button 146.

Figure 6:
FIG. 6 depicts the display of FIG. 3 configured for displaying a report of the test performed of FIG. 4.

With respect to FIG. 6, the report 144 may be generated to be displayed on the user interface 129. In one embodiment, the report may contain the identifying information of the test device 102 and the date of calibration of the test device 102. In one embodiment, and with respect to FIG. 4, examples of the unique identifying information of the test equipment 102 include element 170 (ST1879), element 172 (SC07673), and element 174 (OX01678). The report 144 may further provide, for example, which profile was used, the time and date of testing, what tests were run, what the pass/fail criteria were, and what the results of the test were. In one embodiment, the user 131 may enter any notes to be stored at the computing device 106 by selecting an add notes button 156. In one embodiment, the user 131 may copy and paste a report 144 to another window, such as Word document, database, or email, and the like. The report 144 may also be stored on the user computing device 106. In one embodiment, up to 1000 reports may be stored on the user computing device 106. Furthermore, the user 131 may email the report 144 as a PDF by selecting a share PDF button 150. In one embodiment, the generated report may be stored at the remote server 109.

Figure 7:
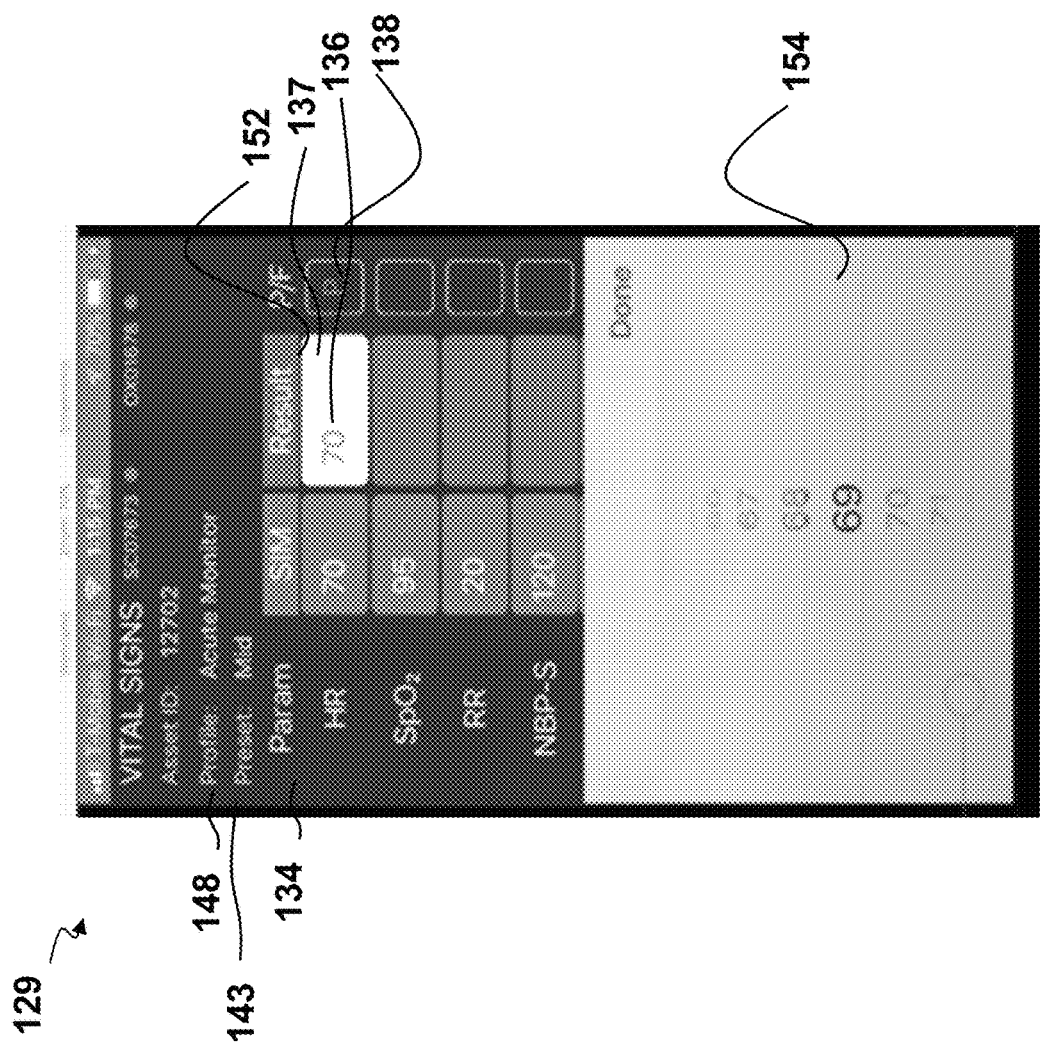
FIG. 7 depicts the display of FIG. 3 configured for entering of test parameter values related to a test device.

With respect to FIG. 7, the user 131 may wish to perform a different set of tests in order to test additional aspects of a medical device, such as medical device 104. In one embodiment, the user may select a new profile to run tests to ensure the medical device 104 is properly tracking vital signs of patient. In this example, the profile is an acute monitor profile 148. The profile 148 may have a series of steps or presets and each preset configures all of a set of simulation parameter values 134 that may be under simulation simultaneously. In this example, a preset 143 is set to run test corresponding to the preset "Mid". Therefore, all of the simulation parameter values 134 may be set in parallel so the medical device 102 may perform capture and analysis of simulated parameters in parallel. This may minimize the time that the user 131 needs to wait to observe results. In some embodiments, the selected preset may set two or more simulation parameter values 134 in parallel. In one embodiment, the selected preset may set two simulation parameter values 134 in parallel. In another embodiment, the selected preset may set three or more simulation parameter values 134 in parallel. Some simulations may have overlap that allow for running two or more simulation parameter values 134 in parallel. As a result of setting two or more simulation parameter values 134, the medical device 102 is able to perform, capture and analyze the simulated parameters in parallel. Simulation parameter values 134 may include heart rate (HR), $S_pO_2$, RR, NBP-S, NBP-D, and the like. In one embodiment, completion of a non-invasive blood pressure reading requires inflating the cuff to a minimum pressure and then deflating the cuff, and is detected by the test device 104 and transmitted to the user computing device 106. When the cuff is deflated the reading is complete. Until the reading is complete, the NBP-S and NBP-D determined parameter values 136 may be replaced with a message that reminds the user 131 to start a reading and displays the current cuff pressure, thereby allowing the user 131 to track the progress of the reading. In another embodiment, the user computing device 106 may be notified by the test device 104 when the $S_pO_2$ is connected to the test device 104, thus if the $S_pO_2$ is not connected, the $S_pO_2$ simulated parameter value 134 may be replaced with a message that reminds the user 131 to connect the test device 106.

In one embodiment, if the user 131 is testing a particular device that requires a different set of simulation parameter values 134, the user may override the preset simulation parameter values 134 and manually enter the desired simulation parameter values 134.

Figure 5:
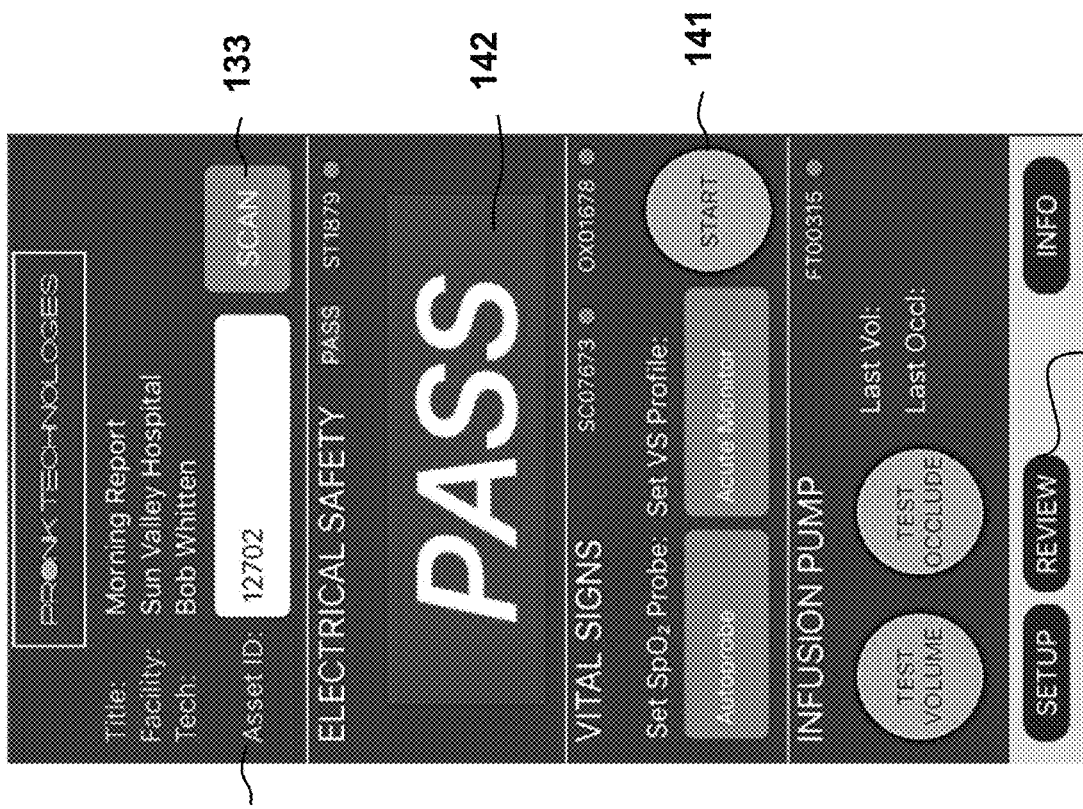
FIG. 5 depicts the display of FIG. 3 configured for displaying a result of the test performed of FIG. 4.

Again, the user 131 may then initiate the tests by selecting a start button 141 (see FIGS. 4 and 5). Selection of the start button 141 causes the processor to execute steps of instructions to generate the profile of tests to be wirelessly transmitted with the transceiver 112 to the test device 102. The processor 105 of the test device 102 may then execute steps to run the profile of tests on the medical device 104. In one embodiment, the results may be read off of the test device 102 and the user 131 may then manually enter the results for each parameter at the computing device 106 to be displayed on the user interface 129. More specifically, the user may select a result button, such as result button 137 from a results column 152 related to a heart rate (HR) simulation parameter value. The user 131 may then enter a test parameter result 136 (e.g., HR of "70" in this instance) from the test device 102 with the touch keyboard 153 (see FIG. 3) or by selecting a value from a drop-down list 154.

Figure 8:
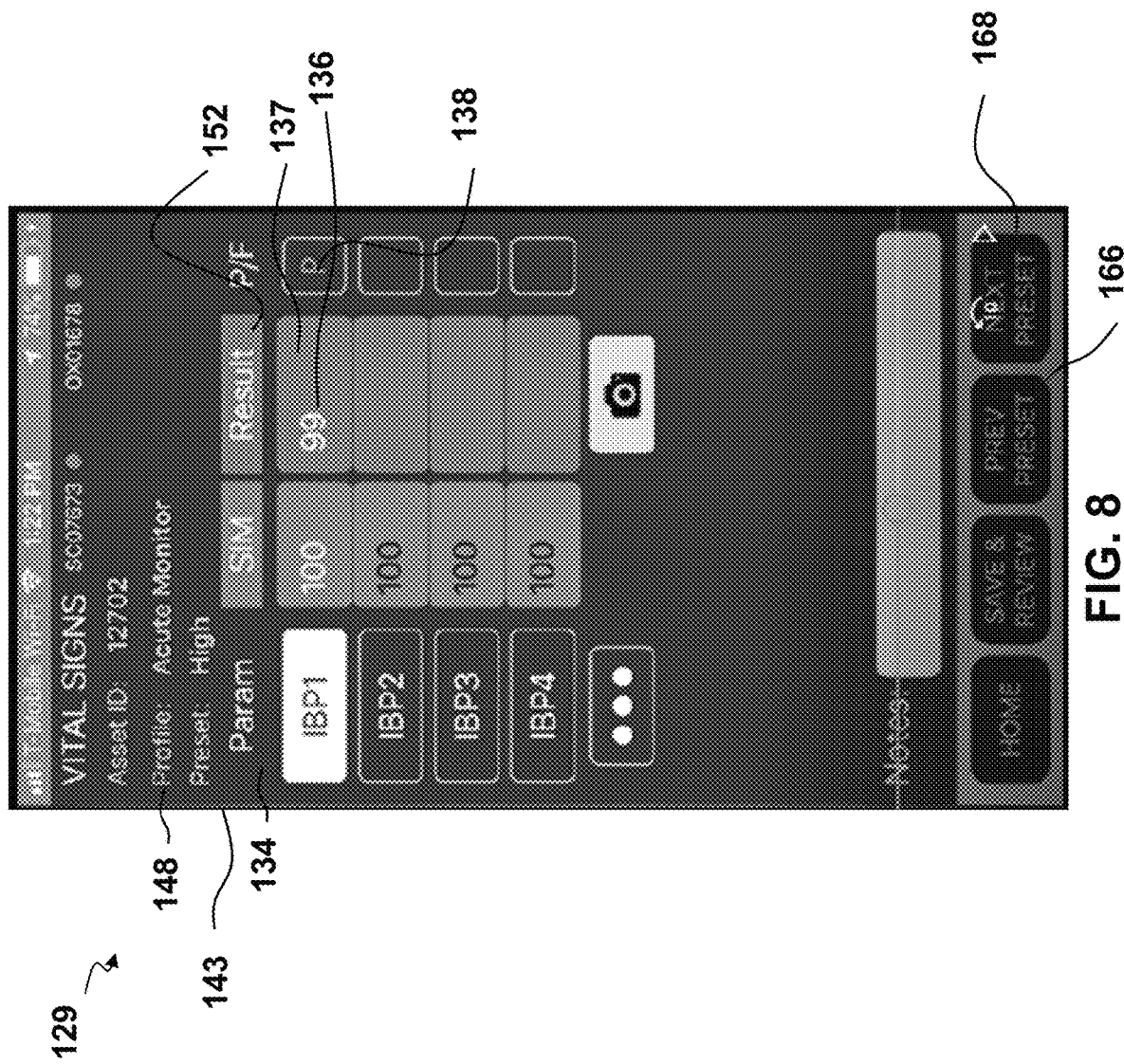
FIG. 8 depicts the display of FIG. 3 configured for displaying test results from testing with an alternative preset.

With respect to FIG. 8, the user 131 may wish to perform a different set of steps or presets than previously ran, such as a preset 143 set to "Mid" or "High" related to the profile 148 (the same profile of FIG. 7). The "Mid" or "High" preset of preset 143 configures all of a set of simulation parameter values 134 that may be under simulation simultaneously. In this embodiment, the simulation parameter values 134 are different than the simulation parameter values 134 of the example of FIG. 7, because a new preset (e.g., "Mid") is under simulation. Once again, all of the simulation parameter values 134 may be set in parallel so operator interaction and wait times are minimized.

With respect to FIG. 7, the processor 108 is configured to compare the simulation test parameter values 134 with the determined parameter values 136 entered by the user 131. The comparison may be based on pass or fail criteria that may be predetermined within the specific profile being used or the pass or fail criteria may be set by the user 131. In the example of FIG. 7, the simulation parameter value 134 for a heart rate vital sign is 70 and the determined parameter value 136 from the test device 102 entered manually by the user 131 is also 70. This result meets the pass criteria and is designated as a "P" in a pass/fail result box 138.

Again, a report 144 may be generated to be displayed on the user interface 129. In one embodiment, the report may contain the identifying information of the test equipment 102 and the date of calibration of the test device 102. The report 144 may further provide which profile was used, the time and date of testing, what tests were run, what the pass/fail criteria were, and what the results of the test were. In one embodiment, the user 131 may enter any notes to be stored at the computing device 106 by selecting an add notes button 156. In one embodiment, the user 131 may copy and paste a report 144 to another window, such as Word document, and the like. The report 144 may also be stored on the user computing device 106. In one embodiment, up to 1000 reports may be stored on the user computing device 106. Furthermore, the user 131 may email the report 144 as a PDF by selecting a share PDF button 150.

Figure 9:
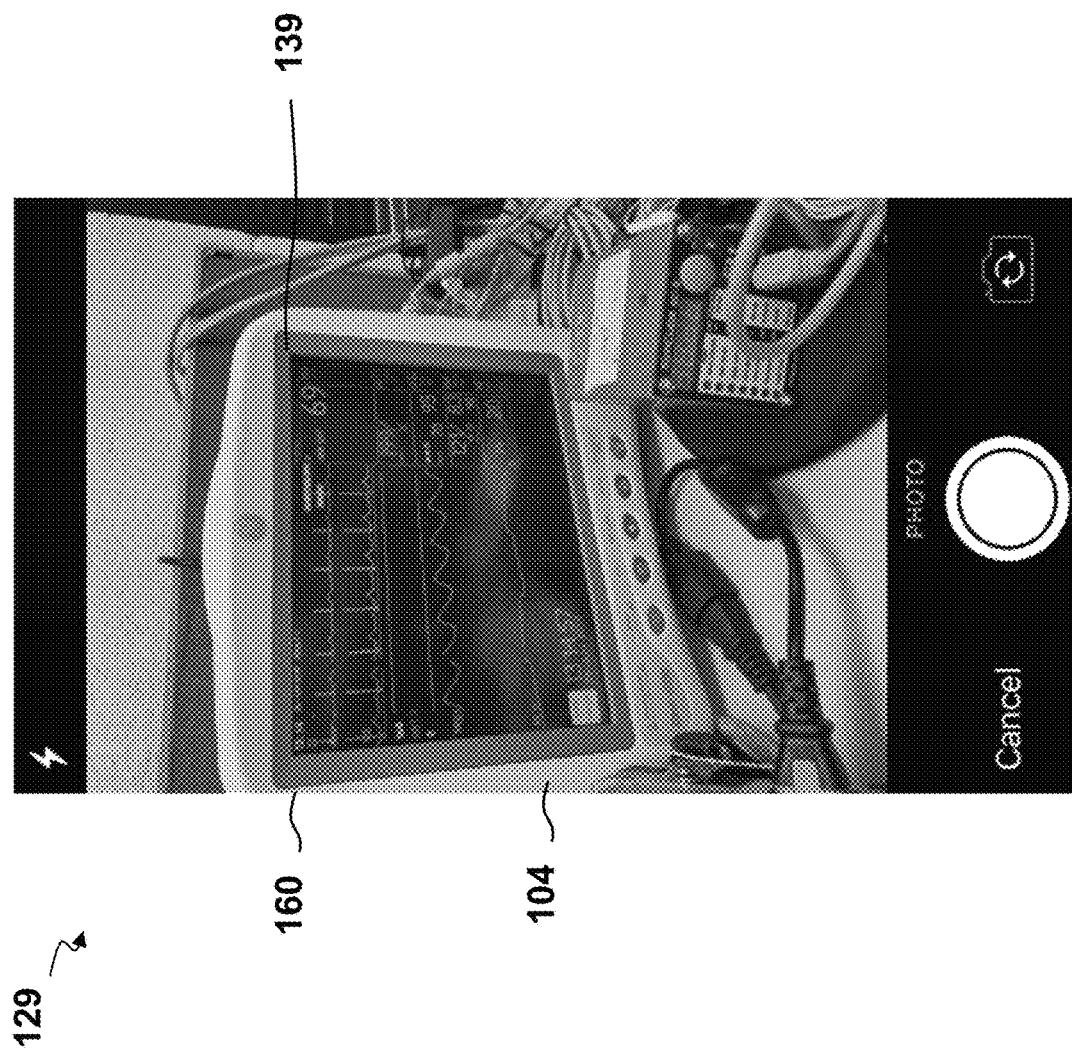
FIG. 9 depicts an image captured by the user computing device of FIG. 2 displayed on the display of FIG. 3.

To provide further documentation, the user 131 may select the camera button 158 (see FIG. 6) to capture an image 160 of the determined parameter values 134 that may be displayed as captured parameter values 139 on the medical device 104, as shown in FIG. 9. The captured image 160 with the captured parameter values 139 may be stored on the user computing device 106 or on the remote server 109.

In one embodiment, the captured image 160 may be used to populate the determined parameter values 136. For example, the user 131 may be prompted to tap the location of each needed determined parameter value 136 present in the captured image 160. Recognition software may be applied to find the determined parameter value 136 within the captured image 160.

In one embodiment, the relative location of each determined parameter value 136 in the captured image 160 may be retained so that when the user 131 proceeds to a next preset 168 (see FIG. 8) and a new captured image is generated, recognition software has pre-determined where to find the determined parameter value 136 in the new captured image, and the user need not locate the captured parameter values 139 in the captured image 160 manually.

In one embodiment, the user computing device 106 may force each simulated parameter value 134 in the initial preset to be numerically far from each other (see FIG. 7). For example, HR and NBP-D might normally be close to each other in value, but they may be configured so that this is not the case. Recognition software may then use the fact that each determined parameter value 136 should be close to its simulated parameter value 134 to figure out the location of each determined parameter value 136 in the captured image 160.

In one embodiment, the user computing device 106 may track the relative location of each determined parameter value 136 in the captured image 160 associated with each preset, such as presets "Mid" and "High" of FIGS. 7 and 8, respectively. If a specific determined parameter value 136 seems to appear in a specific screen location in one preset's captured image and in a different location in another preset's captured image, then the recognition software may have made an error in one of the images. This error may be flagged for the user 131 to fix; however, if there are enough images within the profile for the error may be automatically fixed by the user computing device 106.

In one embodiment, it may be desired to use camera images rather than manual entry of data as a quality assurance step to ensure operators are not simply entering results without actually performing tests. However, images may be falsified by re-using camera images or by using the camera to take images of hardcopy print-outs of previously gathered screen images. In some instances, the numerical values displayed may be mainly fixed; however, there may also be a waveform display which changes in real time. Images captured at different points in time will naturally produce variances in waveform. For example, if the camera captures two images, separated in time by a brief amount of time, such as several hundred milliseconds (rather than a single image) recognition software may verify that the waveform display in the images has indeed changed as expected. Re-using of the same images would yield no variance in the waveform, making it a far greater challenge to falsify images.

In one embodiment, no determined parameter values 134 are to be entered by the user 131. Instead, a text prompt may appear on the display 129 to prompt the user 131 to take an action or observe a property of the medical device 104 (e.g. "check device is clean"). In one embodiment, the text prompt is an abbreviated message and the user 131 may press the text prompt causing the text prompt to expand and display a more detailed text message.

In some embodiments, fail safes are in place to detect human error. For example, a manager may be automatically notified if a user has been entering determined parameter values 134 too rapidly. In another example, a manager may be automatically notified if a user has been entering determined parameter values 134 that consistently exactly match the default simulation parameter values 132.

In one embodiment, the system may generate an alert notification if one or more parameter values are entered faster than a predetermined limit thereby avoiding user error. For example, the time to complete testing may have a minimum time and any values entered before this minimum time may be used to generate an alert for human error, entering incorrect parameter values, or the like. In one embodiment, the system may generate an alert notification if the received one or more parameter values are within a predetermined limit of one or more default simulation parameter values thereby avoiding user error. The system may detect if the entered simulation parameter values are too close to the default simulation parameter values, such as may occur if a user is entering incorrect information or using information from a previous simulation. In some embodiments, the alert may be displayed to a user performing the test so as to take corrective action. In other embodiments, the alert may be sent to a cloud server, manager user device, or the like to inform a manager that an error has occurred and to allow the manager to take corrective action.

Figure 10:
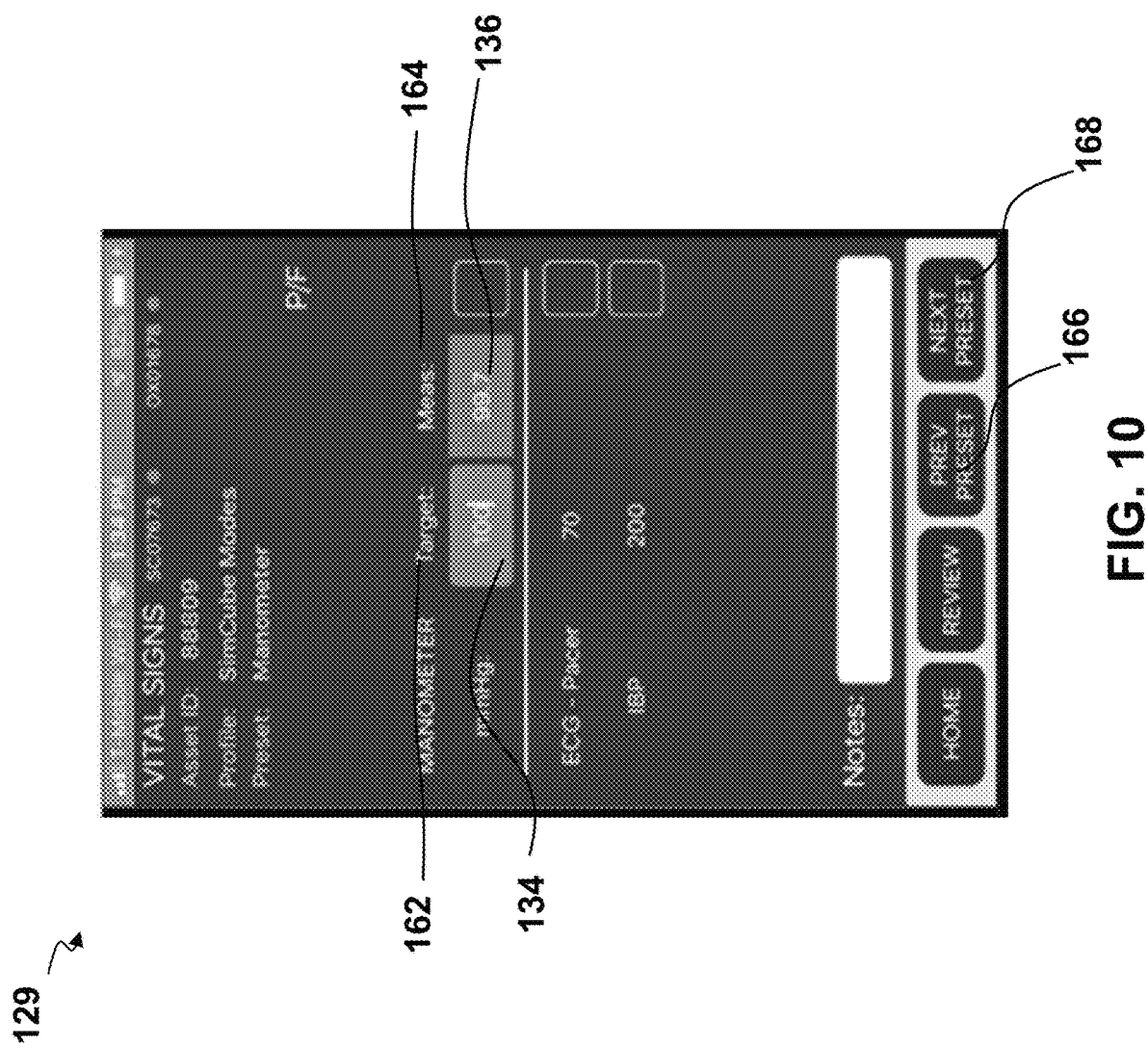
FIG. 10 depicts the display of FIG. 3 configured for displaying test results from testing of an alternative test device.

With respect to FIG. 10, a manometer device is tested. In one embodiment, selection of the profile (e.g., "SimCube Modes") may automatically populate a target field 162 with the simulation parameter value 134 to be tested. In this example, upon testing of the medical device with the test device, the test device wirelessly transmits the measured parameter value 134 to the user device 106. As such, the user 131 does not manually enter the determined parameter value 136; rather the determined parameter value 136 may be sourced directly from the test device and are directly populated into a measured field 164.

The processor 108 is configured to compare the simulation test parameter values 134 with the determined parameter values 136 automatically populated into the measured field 164. The comparison may be based on a pass or fail criteria that may be predetermined within the specific profile being used or the pass or fail criteria may be set by the user 131.

System embodiments include computing devices such as a server computing device, a buyer computing device, and a seller computing device, each comprising a processor and addressable memory and in electronic communication with each other. The embodiments provide a server computing device that may be configured to: register one or more buyer computing devices and associate each buyer computing device with a buyer profile; register one or more seller computing devices and associate each seller computing device with a seller profile; determine search results of one or more registered buyer computing devices matching one or more buyer criteria via a seller search component. The service computing device may then transmit a message from the registered seller computing device to a registered buyer computing device from the determined search results and provide access to the registered buyer computing device of a property from the one or more properties of the registered seller via a remote access component based on the transmitted message and the associated buyer computing device; and track movement of the registered buyer computing device in the accessed property via a viewer tracking component. Accordingly, the system may facilitate the tracking of buyers by the system and sellers once they are on the property and aid in the seller's search for finding buyers for their property. The figures described below provide more details about the implementation of the devices and how they may interact with each other using the disclosed technology.

Figure 11:
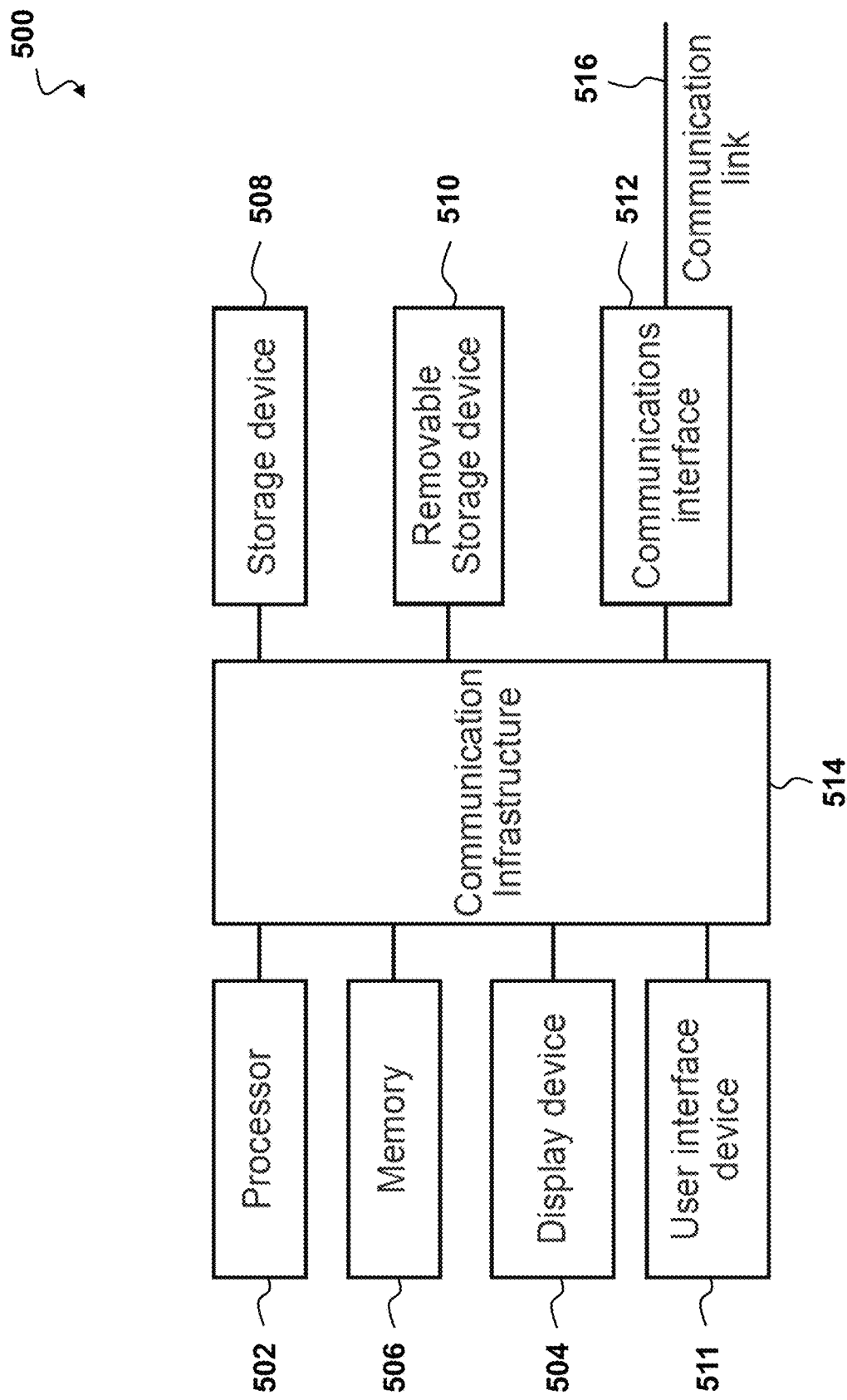
FIG. 11 shows a high-level block diagram and process of a computing system for implementing an embodiment of the system and process.

FIG. 11 is a high-level block diagram 500 showing a computing system comprising a computer system useful for implementing an embodiment of the system and process, disclosed herein. Embodiments of the system may be implemented in different computing environments. The computer system includes one or more processors 502, and can further include an electronic display device 504 (e.g., for displaying graphics, text, and other data), a main memory 506 (e.g., random access memory (RAM)), storage device 508, a removable storage device 510 (e.g., removable storage drive, a removable memory module, a magnetic tape drive, an optical disk drive, a computer readable medium having stored therein computer software and/or data), user interface device 511 (e.g., keyboard, touch screen, keypad, pointing device), and a communication interface 512 (e.g., modem, a network interface (such as an Ethernet card), a communications port, or a PCMCIA slot and card). The communication interface 512 allows software and data to be transferred between the computer system and external devices. The system further includes a communications infrastructure 514 (e.g., a communications bus, cross-over bar, or network) to which the aforementioned devices/modules are connected as shown.

Information transferred via communications interface 514 may be in the form of signals such as electronic, electromagnetic, optical, or other signals capable of being received by communications interface 514, via a communication link 516 that carries signals and may be implemented using wire or cable, fiber optics, a phone line, a cellular/mobile phone link, an radio frequency (RF) link, and/or other communication channels. Computer program instructions representing the block diagram and/or flowcharts herein may be loaded onto a computer, programmable data processing apparatus, or processing devices to cause a series of operations performed thereon to produce a computer implemented process.

Embodiments have been described with reference to flowchart illustrations and/or block diagrams of methods, apparatus (systems) and computer program products according to embodiments. Each block of such illustrations/diagrams, or combinations thereof, can be implemented by computer program instructions. The computer program instructions when provided to a processor produce a machine, such that the instructions, which execute via the processor, create means for implementing the functions/operations specified in the flowchart and/or block diagram. Each block in the flowchart/block diagrams may represent a hardware and/or software module or logic, implementing embodiments. In alternative implementations, the functions noted in the blocks may occur out of the order noted in the figures, concurrently, etc.

Computer programs (e.g., computer control logic) are stored in main memory and/or secondary memory. Computer programs may also be received via a communications interface 512. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system.

Figure 12:
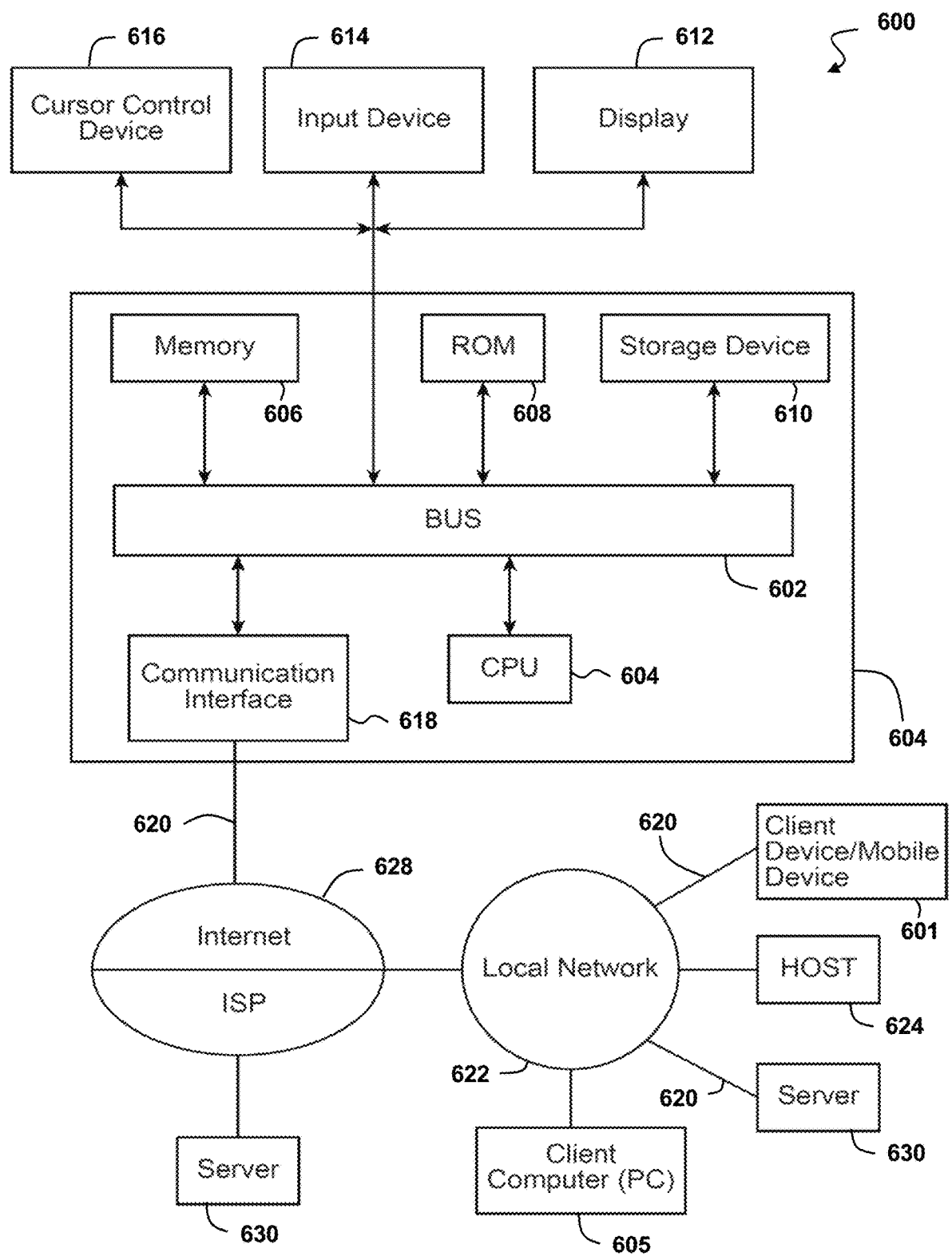
FIG. 12 shows a block diagram and process of an exemplary system in which an embodiment may be implemented.

FIG. 12 shows a block diagram of an example system 600 in which an embodiment may be implemented. The system 600 includes one or more client devices 601 such as consumer electronics devices, connected to one or more server computing systems 630. A server 630 includes a bus 602 or other communication mechanism for communicating information, and a processor (CPU) 604 coupled with the bus 602 for processing information. The server 630 also includes a main memory 606, such as a random access memory (RAM) or other dynamic storage device, coupled to the bus 602 for storing information and instructions to be executed by the processor 604. The main memory 606 also may be used for storing temporary variables or other intermediate information during execution or instructions to be executed by the processor 604. The server computer system 630 further includes a read only memory (ROM) 608 or other static storage device coupled to the bus 602 for storing static information and instructions for the processor 604. A storage device 610, such as a magnetic disk or optical disk, is provided and coupled to the bus 602 for storing information and instructions. The bus 602 may contain, for example, thirty-two address lines for addressing video memory or main memory 606. The bus 602 can also include, for example, a 32-bit data bus for transferring data between and among the components, such as the CPU 604, the main memory 606, video memory and the storage 610. Alternatively, multiplex data/address lines may be used instead of separate data and address lines.

The server 630 may be coupled via the bus 602 to a display 612 for displaying information to a computer user. An input device 614, including alphanumeric and other keys, is coupled to the bus 602 for communicating information and command selections to the processor 604. Another type or user input device comprises cursor control 616, such as a mouse, a trackball, or cursor direction keys for communicating direction information and command selections to the processor 604 and for controlling cursor movement on the display 612.

According to one embodiment, the functions are performed by the processor 604 executing one or more sequences of one or more instructions contained in the main memory 606. Such instructions may be read into the main memory 606 from another computer-readable medium, such as the storage device 610. Execution of the sequences of instructions contained in the main memory 606 causes the processor 604 to perform the process steps described herein. One or more processors in a multi-processing arrangement may also be employed to execute the sequences of instructions contained in the main memory 606. In alternative embodiments, hard-wired circuitry may be used in place of or in combination with software instructions to implement the embodiments. Thus, embodiments are not limited to any specific combination of hardware circuitry and software.

The terms "computer program medium," "computer usable medium," "computer readable medium", and "computer program product," are used to generally refer to media such as main memory, secondary memory, removable storage drive, a hard disk installed in hard disk drive, and signals. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allow a computer to read such computer readable information. Computer programs (also called computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor multi-core processor to perform the features of the computer system. Accordingly, such computer programs represent controllers of the computer system.

Generally, the term "computer-readable medium" as used herein refers to any medium that participated in providing instructions to the processor 604 for execution. Such a medium may take many forms, including but not limited to, non-volatile media, volatile media, and transmission media. Non-volatile media includes, for example, optical or magnetic disks, such as the storage device 610. Volatile media includes dynamic memory, such as the main memory 606. Transmission media includes coaxial cables, copper wire and fiber optics, including the wires that comprise the bus 602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, any other memory chip or cartridge, a carrier wave as described hereinafter, or any other medium from which a computer can read.

Various forms of computer readable media may be involved in carrying one or more sequences of one or more instructions to the processor 604 for execution. For example, the instructions may initially be carried on a magnetic disk of a remote computer. The remote computer can load the instructions into its dynamic memory and send the instructions over a telephone line using a modem. A modem local to the server 630 can receive the data on the telephone line and use an infrared transmitter to convert the data to an infrared signal. An infrared detector coupled to the bus 602 can receive the data carried in the infrared signal and place the data on the bus 602. The bus 602 carries the data to the main memory 606, from which the processor 604 retrieves and executes the instructions. The instructions received from the main memory 606 may optionally be stored on the storage device 610 either before or after execution by the processor 604.

The server 630 also includes a communication interface 618 coupled to the bus 602. The communication interface 618 provides a two-way data communication coupling to a network link 620 that is connected to the world wide packet data communication network now commonly referred to as the Internet 628. The Internet 628 uses electrical, electromagnetic or optical signals that carry digital data streams. The signals through the various networks and the signals on the network link 620 and through the communication interface 618, which carry the digital data to and from the server 630, are exemplary forms or carrier waves transporting the information.

In another embodiment of the server 630, interface 618 is connected to a network 622 via a communication link 620. For example, the communication interface 618 may be an integrated services digital network (ISDN) card or a modem to provide a data communication connection to a corresponding type of telephone line, which can comprise part of the network link 620. As another example, the communication interface 618 may be a local area network (LAN) card to provide a data communication connection to a compatible LAN. Wireless links may also be implemented. In any such implementation, the communication interface 618 sends and receives electrical electromagnetic or optical signals that carry digital data streams representing various types of information.

The network link 620 typically provides data communication through one or more networks to other data devices. For example, the network link 620 may provide a connection through the local network 622 to a host computer 624 or to data equipment operated by an Internet Service Provider (ISP). The ISP in turn provides data communication services through the Internet 628. The local network 622 and the Internet 628 both use electrical, electromagnetic or optical signals that carry digital data streams. The signals through the various networks and the signals on the network link 620 and through the communication interface 618, which carry the digital data to and from the server 630, are exemplary forms or carrier waves transporting the information.

The server 630 can send/receive messages and data, including e-mail, program code, through the network, the network link 620 and the communication interface 618. Further, the communication interface 618 can comprise a USB/Tuner and the network link 620 may be an antenna or cable for connecting the server 630 to a cable provider, satellite provider or other terrestrial transmission system for receiving messages, data and program code from another source.

The example versions of the embodiments described herein may be implemented as logical operations in a distributed processing system such as the system 600 including the servers 630. The logical operations of the embodiments may be implemented as a sequence of steps executing in the server 630, and as interconnected machine modules within the system 600. The implementation is a matter of choice and can depend on performance of the system 600 implementing the embodiments. As such, the logical operations constituting said example versions of the embodiments are referred to for e.g., as operations, steps or modules.

Similar to a server 630 described above, a client device 601 can include a processor, memory, storage device, display, input device and communication interface (e.g., e-mail interface) for connecting the client device to the Internet 628, the ISP, or LAN 622, for communication with the servers 630.

The system 600 can further include computers (e.g., personal computers, computing nodes) 605 operating in the same manner as client devices 601, where a user can utilize one or more computers 605 to manage data in the server 630.

Figure 13:
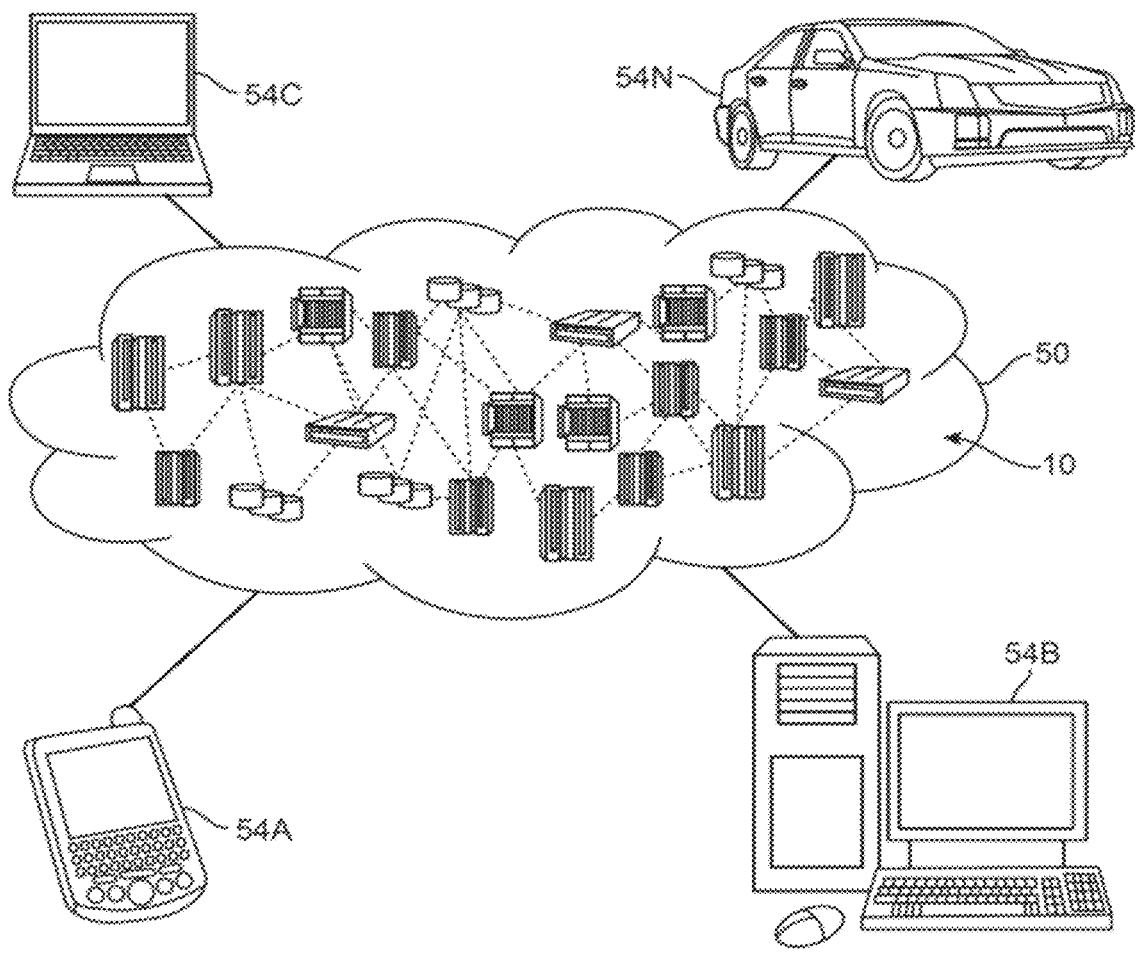
FIG. 13 depicts a cloud computing environment for implementing an embodiment of the system and process disclosed herein.

Referring now to FIG. 13, illustrative cloud computing environment 50 is depicted. As shown, cloud computing environment 50 comprises one or more cloud computing nodes 10 with which local computing devices used by cloud consumers, such as, for example, personal digital assistant (PDA), smartphone, smart watch, set-top box, video game system, tablet, mobile computing device, or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 13 are intended to be illustrative only and that computing nodes 10 and cloud computing environment 50 can communicate with any type of computerized device over any type of network and/or network addressable connection (e.g., using a web browser).

It is contemplated that various combinations and/or subcombinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention is herein disclosed by way of examples and should not be limited by the particular disclosed embodiments described above.

What is claimed is:

1. A system for testing medical devices comprising:
   a test device configured for testing a medical device; and
   a user computing device in communication with the test device, wherein the user computing device comprises a processor having addressable memory, wherein the processor is configured to:
   receive an ID of the medical device to be tested;
   select a profile associated with the received ID of the medical device, wherein the selected profile comprises one or more tests to execute with the test device on the medical device;
   select a preset associated with the selected profile, wherein the selected preset sets two or more simulation parameter values in parallel thereby the medical device performs, capture and analysis of simulated parameters in parallel;
   initiate testing of the medical device by the test device;
   receive one or more parameter values from the test device based on test information results;
   determine a test result based on pass criteria, wherein the determination is based on a comparison of the received one or more parameter values to the one or more simulation parameter values of the preset; and
   generate an alert notification if the received one or more parameter values are entered faster than a predetermined limit thereby avoiding user error.

2. The system of claim 1, wherein the test device further comprises a transceiver for communicating with the user computing device.

3. The system of claim 1, wherein initiating testing of the medical device by the test device further comprises simulating a patient's vital signs.

4. The system of claim 3, wherein the simulated patient vital signs comprise at least one of: temperature, cardiac output (CO), heart rate (HR), $S_pO_2$, RR, IBP-S, IBP-D, NBP-S, and NBP-D.

5. The system of claim 1, wherein the pass criteria is based on a location of the medical device to be tested.

6. The system of claim 5, wherein the location of the medical device to be tested is in at least one of: an area near patients and an area away from patients.

7. The system of claim 1, wherein receiving the ID of the medical device to be tested comprises the processor being further configured to:
   perform an optical scan of a unique identifier corresponding to the ID of the medical device to be tested, wherein the unique identifier comprises at least one of: a barcode and a QR code.

8. The system of claim 1, wherein at least one test of the one or more tests to run of the selected profile is an electrical safety test.

9. The system of claim 1, wherein the selected profile is a new profile.

10. The system of claim 1, wherein the processor is further configured to:
    display the determined test result on a user interface of the user computing device.

11. The system of claim 1, wherein the processor is further configured to:
    generate a report based on the determined test result.

12. The system of claim 11, wherein the generated report further comprises: identifying information of the tested medical device and a calibration date of the tested medical device.

13. The system of claim 12, wherein the generated report further comprises: the selected profile, a time and date the testing of the medical device was initiated, the received one or more parameter values, a pass criteria for each test, and a fail criteria for each test.

14. The system of claim 11, further comprising:
a remote server having a processor with addressable memory, wherein the remote server is in communication with the user computing device, wherein the processor of the remote server is configured to:
receive the generated report; and
store the generated report.

15. The system of claim 1, wherein the processor is further configured to:
capture an image of the received one or more parameter values on a display of the medical device.

16. A The system for testing medical devices comprising:
a test device configured for testing a medical device; and
a user computing device in communication with the test device, wherein the user computing device comprises a processor having addressable memory, wherein the processor is configured to:
receive an ID of the medical device to be tested;
select a profile associated with the received ID of the medical device, wherein the selected profile comprises one or more tests to execute with the test device on the medical device;
select a preset associated with the selected profile, wherein the selected preset sets two or more simulation parameter values in parallel thereby the medical device performs, capture and analysis of simulated parameters in parallel;
initiate testing of the medical device by the test device;
receive one or more parameter values from the test device based on test information results;
determine a test result based on pass criteria, wherein the determination is based on a comparison of the received one or more parameter values to the one or more simulation parameter values of the preset; and
generate an alert notification if the received one or more parameter values are within a predetermined limit of one or more default simulation parameter values thereby avoiding user error.

17. A method comprising:
receiving, by a user computing device having a processor and addressable memory, an ID of the medical device to be tested, wherein the user computing device is in communication with a test device configured for testing a medical device;
selecting, by the processor of the user computing device, a profile associated with the received ID of the medical device, wherein the selected profile comprises one or more tests to run with the test device on the medical device;
selecting, by the processor of the user computing device, a preset associated with the selected profile, wherein the selected preset sets one or more simulation parameter values in parallel thereby the medical device performs capture and analysis of simulated parameters in parallel;
initiating, by the processor of the user computing device, testing of the medical device by the test device;
receiving, by the processor of the user computing device, one or more parameter values based on test information results from the test device;
determining, by the processor of the user computing device, a test result based on pass criteria from a comparison of the received one or more parameter values to the one or more simulation parameter values of the preset;
generating, by the processor of the user computing device, an alert notification if the received one or more parameter values are entered faster than a predetermined limit to avoid user error; and
generating, by the processor of the user computing device, an alert notification if the received one or more parameter values are within a predetermined limit of one or more default simulation parameter values to avoid user error.

18. The method of claim 17, further comprising:
generating, by the processor of the user computing device, a report based on the determined test result, wherein the generated report comprises: identifying information of the tested medical device, a calibration date of the tested medical device, the selected profile, a time and date the testing of the medical device was initiated, the received one or more parameter values, a pass criteria for each test, and a fail criteria for each test.

* * * * *